United States Patent [19]

Nandi et al.

[11] Patent Number: 4,855,300
[45] Date of Patent: Aug. 8, 1989

[54] PHARMACEUTICAL COMPOSITION FOR THE TREATMENT OF CIRCULATORY DISTURBANCES

[75] Inventors: Kumaresh Nandi, Laupheim; Helga Fischer, Oberdischingen; Wilfried Herrmann, Laupheim; Hans Köhne, Obersulmetingen; Wolfgang Lahr, Laupheim; Hein U. Schmersahl, Ehingen; Hatto Walch, Baustetten, all of Fed. Rep. of Germany

[73] Assignee: Dr. Rentschler Arzneimittel GmbH & Co., Laupheim, Fed. Rep. of Germany

[21] Appl. No.: 10,782

[22] Filed: Feb. 4, 1987

[30] Foreign Application Priority Data

Feb. 10, 1986 [DE] Fed. Rep. of Germany ....... 3604149

[51] Int. Cl.$^4$ ...................... A61K 31/44; A61K 31/52
[52] U.S. Cl. .................................. 514/264; 514/356; 514/929
[58] Field of Search .................. 514/356, 264, 929

[56] References Cited

U.S. PATENT DOCUMENTS 3,422,107  1/1969  Mohler et al. ..................... 514/929
4,504,476  3/1985  Schwartz et al. .................. 514/211

OTHER PUBLICATIONS

The Merck Index 10th Ed. (1983) pp. 931, 936, 937, 569, 1025 and 1026.
K. U. Benner, "Klinische Hamorheologie: Grundlagen und Geschichte", GIT Labor-Medizin, 5/85 pp. 295, 296, 300, 301 & 302.
A. Fleckenstein, R. Roskamm, "Consequences of Uncontrolled Calcium Entry and its Prevention with Calcium Antagonists", English Publication of Fleckenstein from European Heart Journal, 4, Supplement H,43–50, 1983, corresponding to the cited article.
R. Muller, Therapiewoche 30, 1980, the relevant passages have been translated into English.
Dettelbach et al., Journal of Clinical Pharmacology, 1985.
Aviado et al., Pharmacotherapy, vol. 4, No. 6, 1984, "Pentoxifylline: A New Drug for the Treatment of Intermittent Claudication".

Primary Examiner—Allen J. Robinson
Attorney, Agent, or Firm—Cohen, Pontani & Lieberman

[57] ABSTRACT

A pharmaceutical combination preparation and method for the treatment of circulatory disturbances comprising a dihydropyridine of the formula

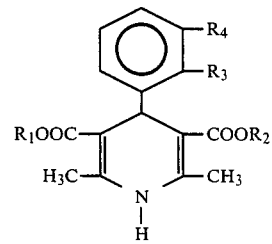

in which $-R_1$, is a $CH_3-O-CH_2-CH_2-$ or $CH_3$ group; $R_2$ is a

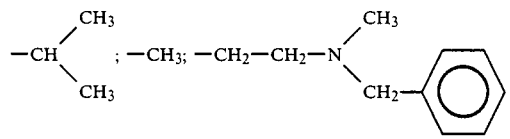

or $CH_3-CH_2-$ group; $R_3$ is 4, $NO_2$ or $CL$; and $R_2$ is $NO_2$, H or $CL$; and pharmaceutically suitable salts thereof; as active substance A and Pentoxifylline as active substance B, the quantity ratios of A:B being from about 1:150 to about 1:2.

7 Claims, 9 Drawing Sheets

Erythrocyte Flexibility
Pentoxifylline

\* p < 0.05
N.S. not significant
Pent. - Pentoxifylline

FIG. 1B

Erythrocyte Flexibility
Nifedipine

* $p < 0.05$

N.S. = not significant    Nif. = Nifedipine

FIG. 1C

Erythrocite Flexibility
% Pentoxifylline + Nifedipine

*p < 0.01            (100% = 0.46)

N.S. = not significant          Pent. = Pentoxifylline

Nif = Nifedipine

FIG. 2B
Erythrocyte Aggregation
Nifedipine (100% = 16.84)

N.S. not significant     Nif. = Nifedipine

FIG. 3A
Platelet Aggregation (ADP-induced)
Pentoxifylline

** p < 0.01
N.S. not significant    Pent. = Pentoxifylline

PHARMACEUTICAL COMPOSITION FOR THE TREATMENT OF CIRCULATORY DISTURBANCES

FIELD OF THE INVENTION

The present invention generally relates to pharmaceutical combination preparations for the treatment of circulatory disturbances. Specifically, the invention relates to a combination drug which is composed of certain dihydropyridines and pharmaceutically acceptable salts thereof and Pentoxifylline.

BACKGROUND OF THE INVENTION

Heretofore, circulatory disturbances exhibiting causally or symptomatically different syndromes have been treated with drugs having specific actions in each case. Circulatory disturbances as general indications of illness are caused, in the view generally held today, on the one hand, by arteriosclerotic constrictions of the blood vessels and, on the other hand, by pathological changes of the blood flow properties, the restricted microcirculation resulting in a deficient blood supply of the tissue.

In general, circulatory disturbances are often accompanied by a restriction of the functionality of all tissues and organ systems. The functions of the heart, brain, eyes, inner ear and muscle tissue, and particularly of the extremities, are especially affected. Diseases of the coronary vessels which can lead, for instance, to myocardial infarction and sudden heart death, such as angina pectoris, are caused, on the one hand, by arteriosclerosis and spasms and, on the other hand, by hypertension combined with an impairment of the blood flow properties. This generally results in a lack of substrate and oxygen. In general, the identical pathogenetic principle applies to circulatory disturbances of the eye, the inner ear and the muscle tissue, the microcirculation being debilitated due to the impaired fluidity of the blood. K. U. Benner, GIT Labor Medizin, 5, 295–302 1985.

According to the modern view, the following clinical pictures result from the interaction between the morphologically modified blood vessel and the pathologically modified blood vessel and the pathologically modified content of the vessel, namely, liquid components (plasma) and corpuscular components (erythrocytes and thrombocytes or platelets). Diseases of the brain include: transitory ischemic attacks (TIA), PRIND (prolonged reversible ischemic neurological deficits), COP (cerebral organic psychosyndrome) with functional deficits all the way to cerebral infarction (apoplexy). Diseases of the vessels include: coronary heart disease, angina pectoris as well as hypertension. The latter is in itself combined with impaired blood flow properties and is additionally considered as risk factor for apoplexy and myocardial infarction. Diseases of the muscles include: intermittent claudication, ulcus cruris, gangrene all the way to necrosis resulting in amputation, and Raynaud's disease. In the eye, the consequences include impaired vision, all the way to blindness. In the ear, the consequences include tinnitus, hearing impairment and sudden decline in hearing including total loss of hearing.

Dihydropyridines having calcium-antagonist effect of the formula:

in which $R_1$ is a $CH_3$—O—$CH_2$—$CH_2$—or—$CH_3$ group; $R_2$ is a or $CH_3$—$CH_2$—group; $R_3$ is H, $NO_2$ or Cl; and $R_4$ is $NO_2$, H or Cl and pharmaceutically acceptable salts thereof; and particularly Nifedipine, Nimodipine, Nitrendipine, Nicardipine and Felodipine are known and used in the treatment of coronary heart diseases (CHD) and/or high blood pressure (hypertension). The effectiveness, particularly in the case of CHD, hypertension and spastic conditions of the smooth muscles, for instance in the case of asthma, spasms of the uterus, etc., of the above mentioned dihydropyridines is based on their selective inhibition of the calcium influx through the cell membrane of the smooth muscles of the vessels, including the coronary vessels, without affecting the concentration of calcium ions in the blood serum See A. Fleckenstein, H. Roskamm, "Calcium-Antagonismus", Springer-Verlag, 1980.

Pentoxifylline is known and described in Federal Republic of Germany Pat. No. 12 35 320. Pentoxifylline is used for treating disturbances of the peripheral and cerebral circulation. It has no pronounced hemodynamic (affecting the blood) or spasmolytic action such as, for instance, the aforementioned dihydropyridines. Pentoxifylline primarily improves the erythrocyte flexibility, reduces the tendency towards erythrocyte aggregation by increasing the CAMP (cyclic adenosinmonophosphate) by inhibiting the phosphodiesterase thereby producing a decrease in the viscosity of the blood. In addition, the thrombocytes or platelet aggregation is reduced and the fibrinogin and plasma viscosity lowered. R. Müller, Therapiewoche 30, 2440–2451 (1980); Aviado, Porter, Pharmacotheraphy Vol. 4, No. 6 (1985); Dettelbach, Aviado, Journ. of Clin. Pharm. 1985, pages 8–26.

BRIEF DESCRIPTION OF THE DRAWINGS

FIG. 2A is a graph illustrating the erythrocyte aggregation of a probe containing only Pentoxifylline;

DESCRIPTION OF THE INVENTION

Although the above mentioned dihydropyridines exhibit a circulation-promoting effect based on a dilating of the vessels, the blood supply of the tissue, however, requires optimal microcirculation which cannot be obtained solely by vasodilation. To this extent, the use of only dihydropyridines does not result in a sufficient therapeutic benefit. In addition, the circulation-promoting effect of the dihydropyridines cannot be utilized due to the required high doses and concomitant side effects.

Furthermore, the so-called steel phenomenon may occur as a reverse effect, i.e. an additional blood deficiency within already deficiently supplied tissues. In addition, dihydropyridines, even applied in customary therapeutic doses, already cause considerable side effects such as headaches, edema of the legs, flushes and reflex tachycardia. At higher doses, a larger decline in blood pressure, below the desired value, must be expected, thereby increasing the blood deficiency as a result of the reduced perfusion pressure, particularly in the cerebral region.

Pentoxifylline does not have a pronounced hemodynamic effect, so that this substance cannot be used in the treatment of coronary heart disease and hypertension. Pentoxifylline is administered orally in daily doses of up to about 1,600 mg and, in indicated cases, even at higher doses, for instance, with simultaneous oral and parenteral therapy, or in individual doses up to 600 mg. As is known, these therapeutically required high doses lead to considerable side effects such as gastrointestinal disturbances, headache, dizziness and disturbances of the central nervous system.

Heretofore, it was unknown that as a result of the specificity of action of individual substances, and in particular of the combination of the above-referenced dihydropyridines and Pentoxifylline, a target-specific combination therapy for the treatment of impaired blood flow properties can be carried out, since up to now dihydropyridines have been used in principle solely as vasodilator and Pentoxifylline has been used only as circulation-promoting agent. (Rote Liste 1985, consecutive Nos. 23063 and 36048, 36049).

It was therefore surprising to find that important parameters of the blood flow properties can be favorably influenced by the substantially simultaneous administration of Pentoxifylline and one or more of the above-mentioned dihydropyridines or pharmaceutically acceptable salts thereof. As is demonstrated below with Nifedipine as illustrative dihydropyridine, the combined effects of the individual substances, namely the reduction of the erythrocyte aggregation, the increase in the erythrocyte flexibility and inhibition of the thrombocyte aggregation surpass by far the effect of the individual substance Pentoxifylline. It is believed that the superadditive or synergistic effect of the combination preparation is ascribable to the dihydropyridine, which by itself exerts no or scarcely any effect on these parameters.

The combination preparations in accordance with the invention which are composed of one of the named dihydropyridines and Pentoxifylline exhibit an unexpected superadditive effect resulting in a marked improvement of the circulation in the more poorly supplied regions.

At the same time, the known vasoprotective effect of the dihydropyridines and the protection of the heart are increased. The present invention permits a therapy for the improvement of the blood flow properties which are in part responsible for or the cause of the diseases discussed above. It is particularly advantageous that due to the superadditive effect of the composition, the doses of the active components can be reduced clearly below those required for the corresponding monotherapy. The lower doses necessarily have a positive effect on the reduction of the side effects described above.

The doses of the individual components forming the basis of the combinations according to the invention should be adapted in individual and daily doses to the nature and severity of the illness. Suitable ratios of dihydropyridine to Pentoxifylline are from about 1:150 to about 1:2. Particularly preferred ratios within this broad range result for individually selected dihydropyridines depending on the effectiveness thereof. Thus, active substance ratios of from about 1:30 to about 1:10 are suitable for the combination of Nifedipine and Pentoxifylline. For the combination of Nimodipine with Pentoxifylline a suitable ratio is from about 1:10 to about 1:4; for Nitrendipine with Pentoxifylline from about 1:100 to about 1:10; for Nicardipine with Pentoxifylline from about 1:30 to about 1:2.5; for Felodipine with Pentoxifylline from about 1:40 to about 1:5. Pharmaceutically suitable salts of the dihydropyridines, as far as formed, can be used in the same ratios.

In addition to the ratios of active substances, the invention is also characterized by the fact that the active substances are administered simultaneously or substantially simultaneously, preferably in a fixed pharmaceutical form. Simultaneously or substantially simultaneously is understood to include the administration of the active substances at the same time, for example, such as the administration of a combination drug in tablet or capsule form, but also includes the sequential administration of the active substances. Thus, the dihydropyridine may be administered concurrently with the Pentoxifylline, or may be administered before or after the Pentoxifylline has been taken. It is critical, however, that the active substances are taken within such a time span so that the described superadditive or synergistic effect is achieved.

Adjuvants such as fillers and binders, vehicles, lubricants and ointments may be added to the active substances as required. Preferred pharmaceutical forms are solid forms for oral administration such as tablets, film tablets and capsules, but also forms for rectal administration such as suppositories. In serious cases, particularly for clinical use, parenteral forms are preferred containing as vehicle diluents, such as, for instance, organic solvents which are compatible with the active substances. Of course, solutions are also suitable as fixed combinations for oral administration, for instance, in the form of drops.

In accordance with the invention, the active substances can also be present in pharmaceutical forms alongside but separate of each other, particularly if the pharmaceutical forms render the administration difficult with respect of the spatial dimension thereof. This is true in particular for oral forms since frequently in the case of older patients there is a dislike for large tablets and capsules. It is only necessary that the separate pharmaceutical forms be administered at the same time or substantially the same time as explained above. Tablets and capsules may also be used. For long term therapy, regular ingestion is determinative of success. Thus, for long term therapy, as a rule, only oral and rectal pharmaceutical forms are suitable, since, insofar as they are present in sealed blisters bearing a number or indication of the day, the patient is able to check the taking thereof and thus assure compliance with the intended therapy.

The administration of the combination preparation of the two substances in accordance with the invention for simultaneous or substantially simultaneous ingestion thus guarantees high patient and therapy compliance.

The favorable effect of the combination preparation of the invention, which exerts a superadditive effect, are shown in the examples described below, carried out with a combination preparation containing Nifedipine and Pentoxifylline. It will be understood that the examples are given for purposes of illustration only, and that the invention is not restricted thereto.

EXAMPLES

Blood was taken from ten patients (condition after cerebral infarction, peripheral occlusive vascular disease, ischemic heart disease). The blood exhibited pathological filterability in accordance with the method of DODDS-DORMANDY, Brit. Med. Journ., Nov. 1979, pages 1186–1187. Criterion for exclusion was an erythrocyte filterability of more than 0.53. It was assured that the patients had not taken any rheologicals or thrombocytes aggregation inhibitors for three days before the sampling of the blood.

Examination Parameters: Erythrocyte flexibility, erythrocyte aggregation, (ADP-induced) thrombocyte aggregation.

Measurement Methods:

1. Erythrocyte Flexibility:

DODDS-DORMANDY filterability method with the use of 5 μm Nucleopor filters.

2. Erythrocyte Aggregation:

Myrenne Aggreometer (Type MA1, Myrenne Company, 5106 Roetgen), method of Kiesewetter et al., Biomed, Technik, 27, page 209, 1982.

3. Thrombocyte Aggregation:

Method of BORN, J. Physiol. 168, pages 178–195 (1963), with the use of a Bio/Data-Thrombocyte Aggregation Profiler (Type Test Preparations 1. Physiological sodium chloride solution (placebo)
2. Pentoxifylline solution, 10 μg/ml
3. Pentoxifylline solution, 1 μg/ml
4. Pentoxifylline solution, 0.1 μg/ml
5. Mixture of a physiological sodium chloride solution ith ethyl alcohol (placebo)
6. Nifedipine solution, 1.5 μg/ml
7. Nifedipine solution, 0.15 μg/ml
8. Nifedipine solution, 0.015 μg/ml;
9. Combination of Solutions 2 and 6
   (10 μg/ml–1.5 μg/ml)
10. Combination of Solutions 3 and 7
    (1 μg/ml–0.15 μg/ml)
11. Combination of Solutions 4 and 8
    (0.1 μg/ml–0.015 μg/ml)

Tests Procedure

For direct comparison, blood specimens were incubated with a mixture of solutions 1 and 5 (placebo) for 30 minutes at 37° C. and measured. In similar fashion, blood specimens were treated by adding the active-substance solutions of the above table, i.e. of the individual active substances and/or their combinations, in each case in the concentrations indicated above.

Preparation of Specimens

In order to obtain platelet-rich plasma for the determination of the inhibition of thrombocyte aggregation, 2.5 ml of blood were centrifuged four times after treatment.

In order to obtain platelet-free plasma for the determination of the erythrocyte flexibility, 10 ml of blood were centrifuged at 3000 G after treatment.

To determine the lowering of erythrocytes aggregation blood was anticoagulated in customary manner. The aggregation was then determined photometrically by adjusted hematocrit to 45% as shear grade to the point at which a complete dispersion of the erythrocyte aggregates takes place (method of Ernst, Labor Praxis in der Medizin, April 1984, pages 19–21).

The determination of the individual parameters was repeated three times in each case.

Method of Evaluation:

The measured data was tested for significance statistically in accordance with the method of WILCOXON+WILCOX.

Results:

The results are shown in the form of the diagrams in FIGS. 1A to 3C.

Figure 1A:
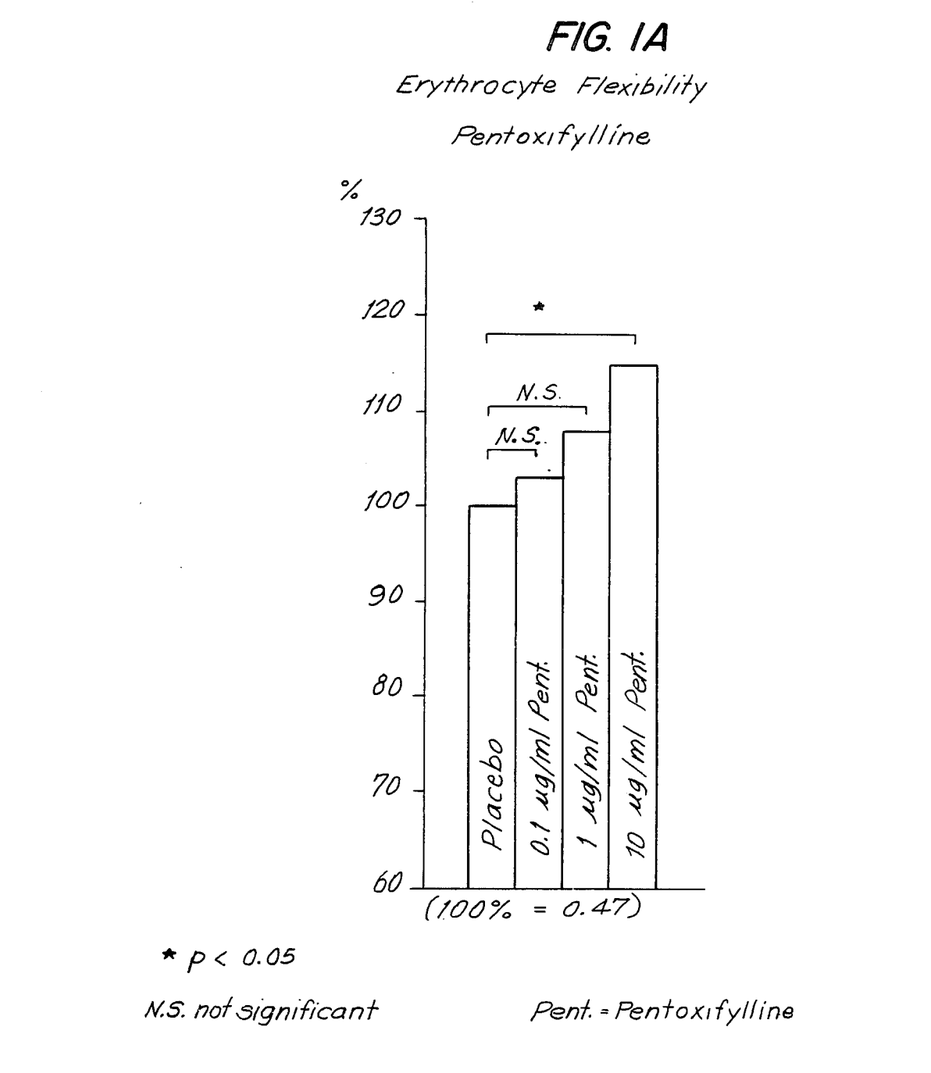
FIG. 1A is a graph illustrating the erythrocyte flexibility of a probe containing only Pentoxifylline.
Figure 1B:
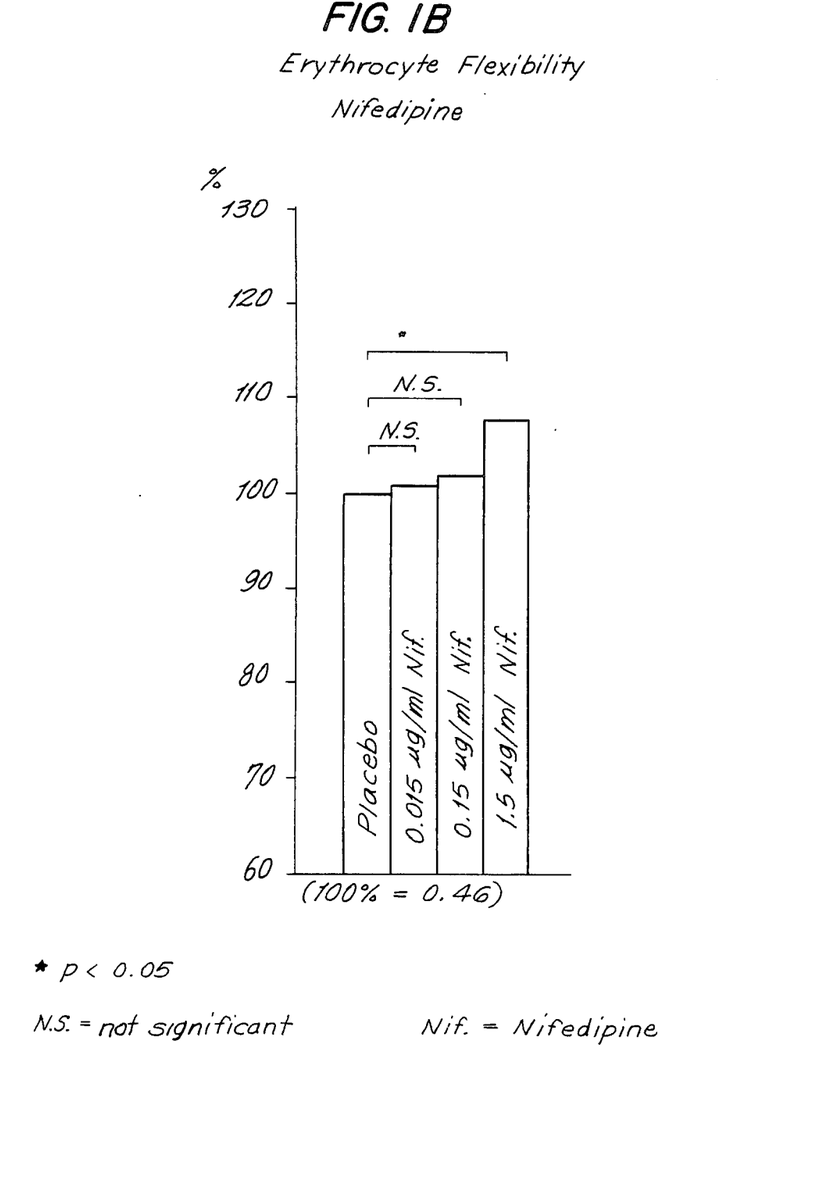
FIG. 1C is a graph illustrating the erythrocyte flexibility of a probe containing both Pentoxifylline and Nifedipine in accordance with the present invention.
Figure 1C:
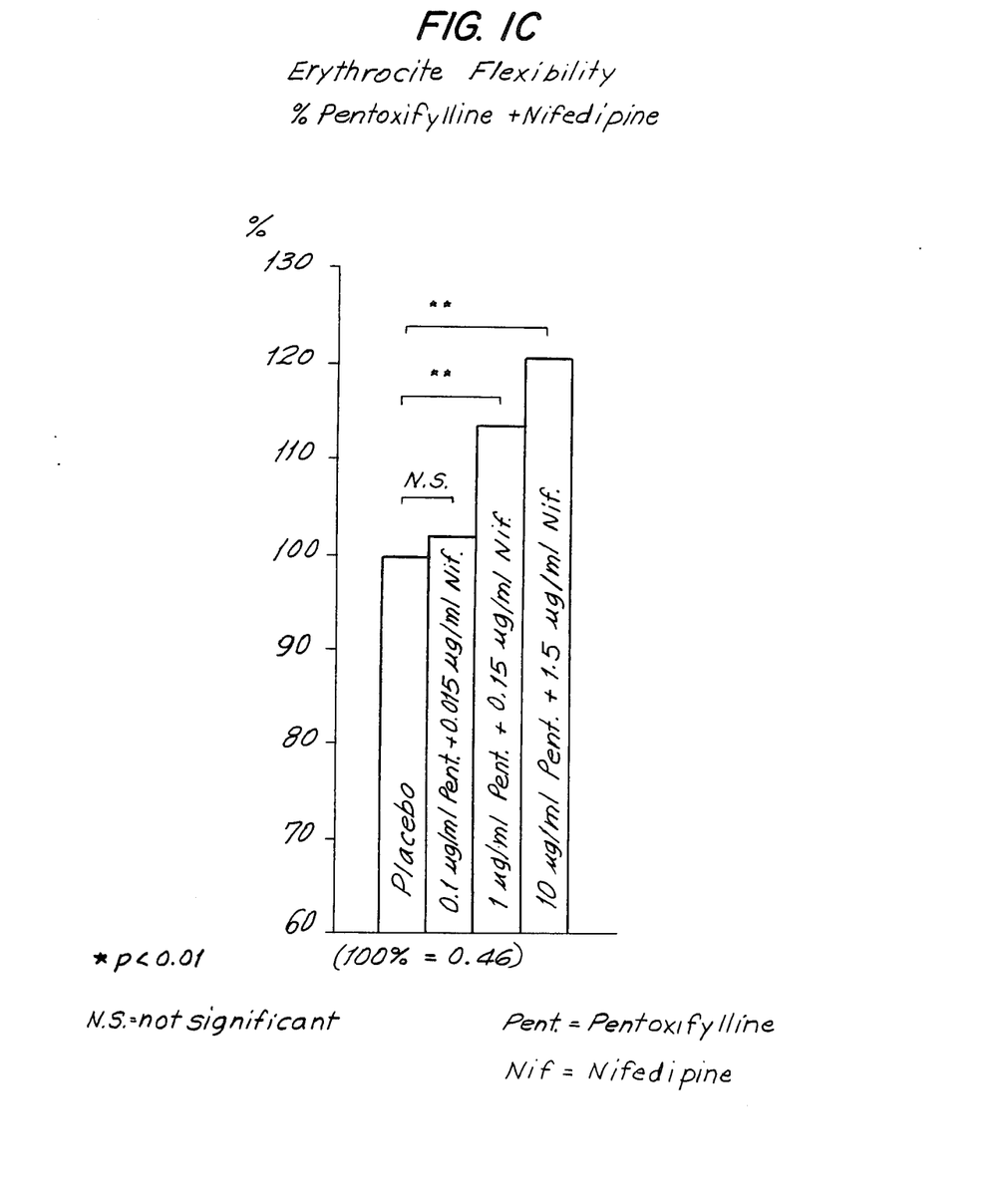
Figure 2A:
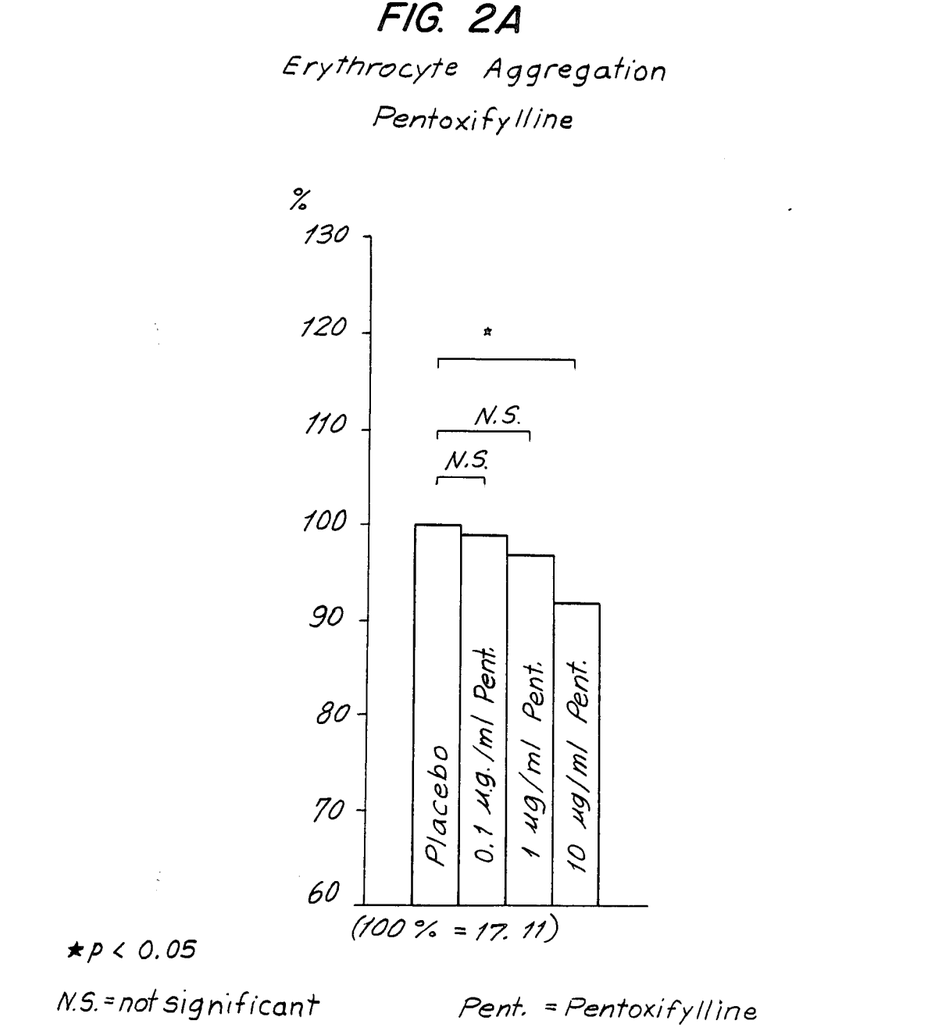
FIG. 2A is a graph illustrating the erythrocyte flexibility of a probe containing only Nifedipine.
Figure 2B:
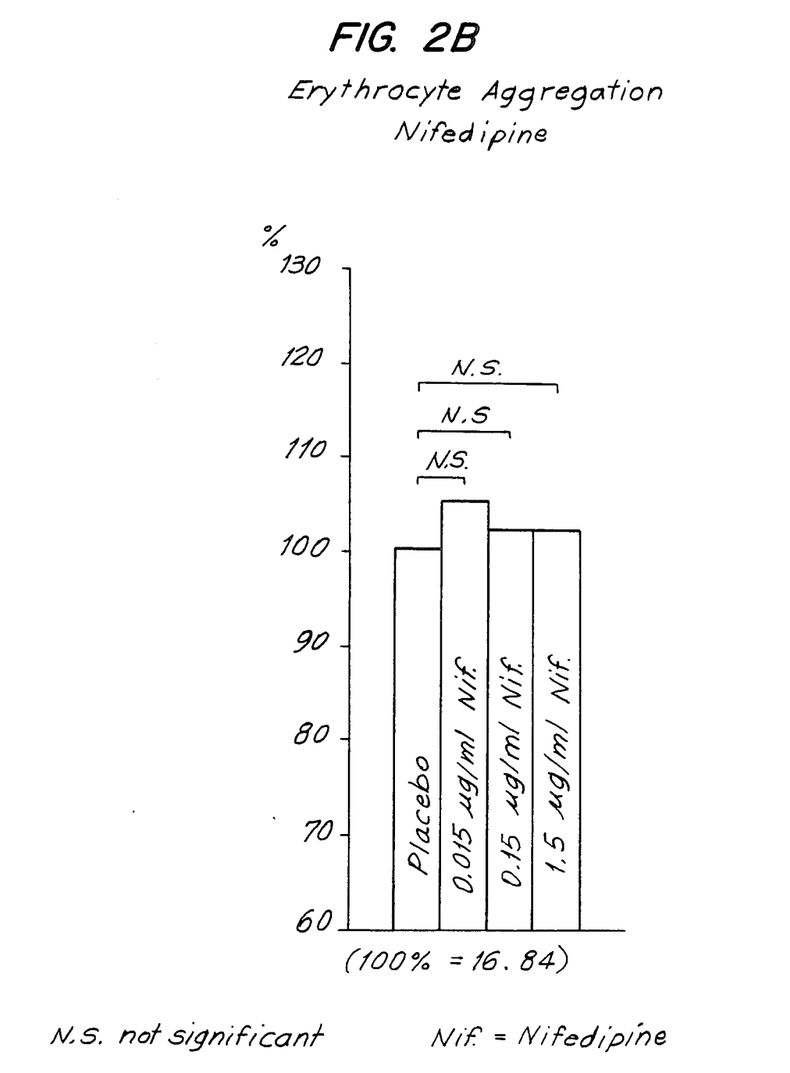
FIG. 2B is a graph illustrating the erythrocyte aggregation of a probe containing only Nifedipine.
Figure 2C:
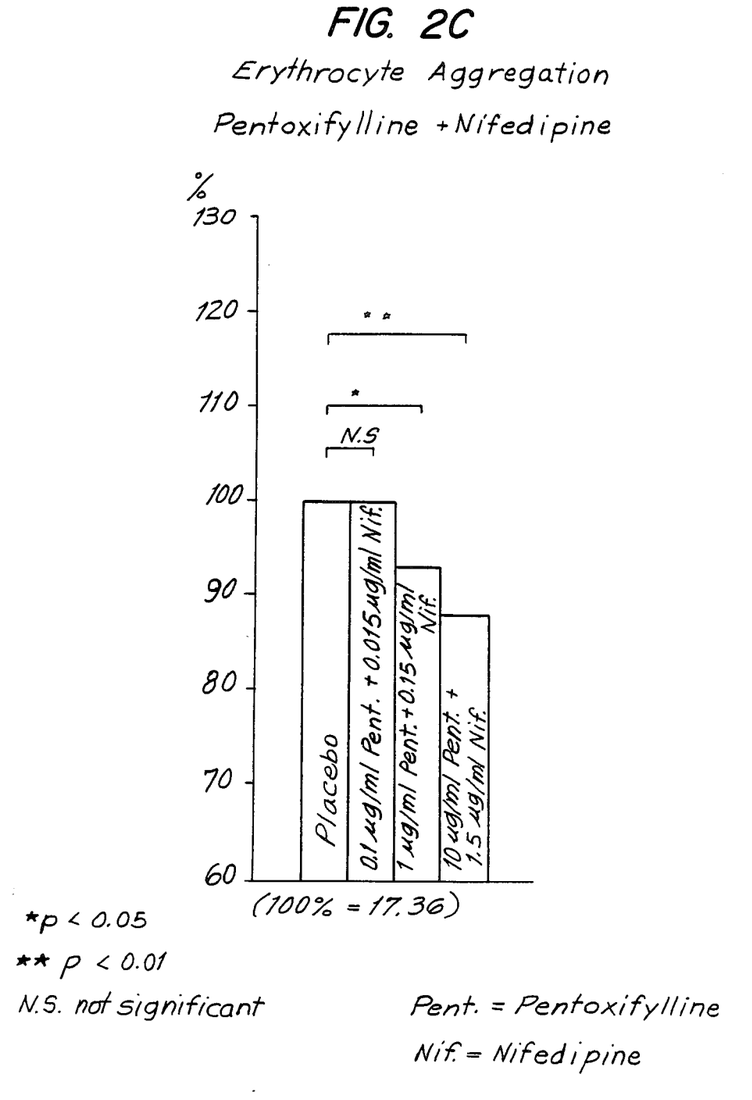
FIG. 2C is a graph illustrating the erythrocyte aggregation of a probe containing both Pentoxifylline and Nifedipine in accordance with the present invention.
Figure 3A:
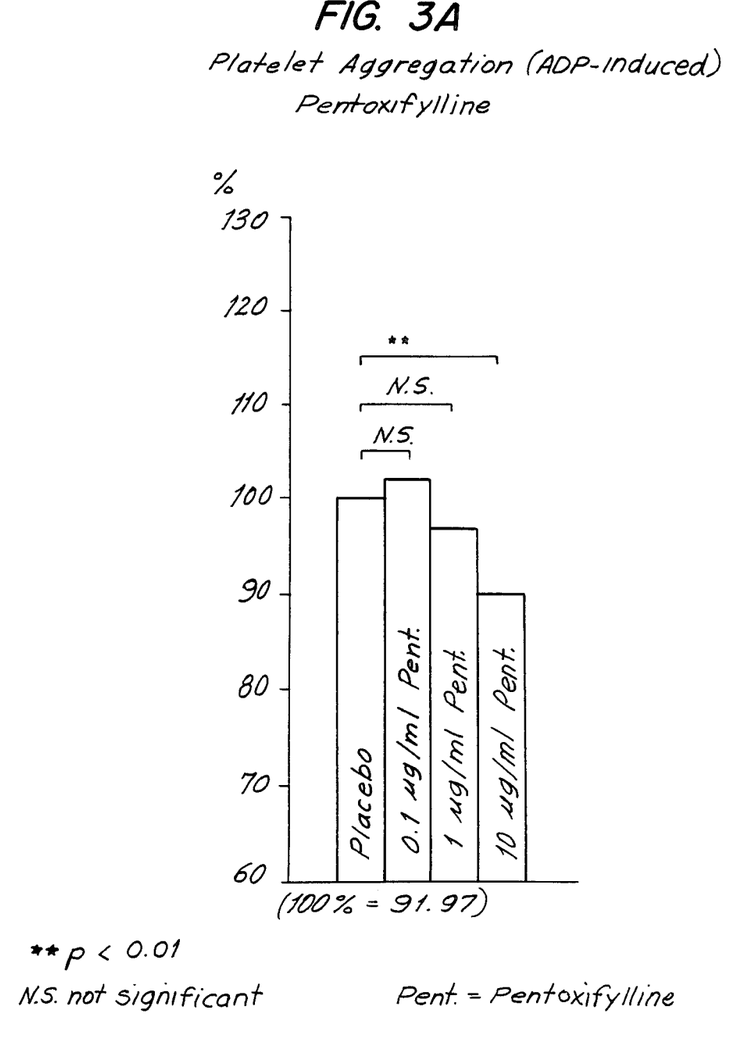
FIG. 3A is a graph illustrating the thrombocyte aggregation of a probe containing only Pentoxifylline.
Figure 3B:
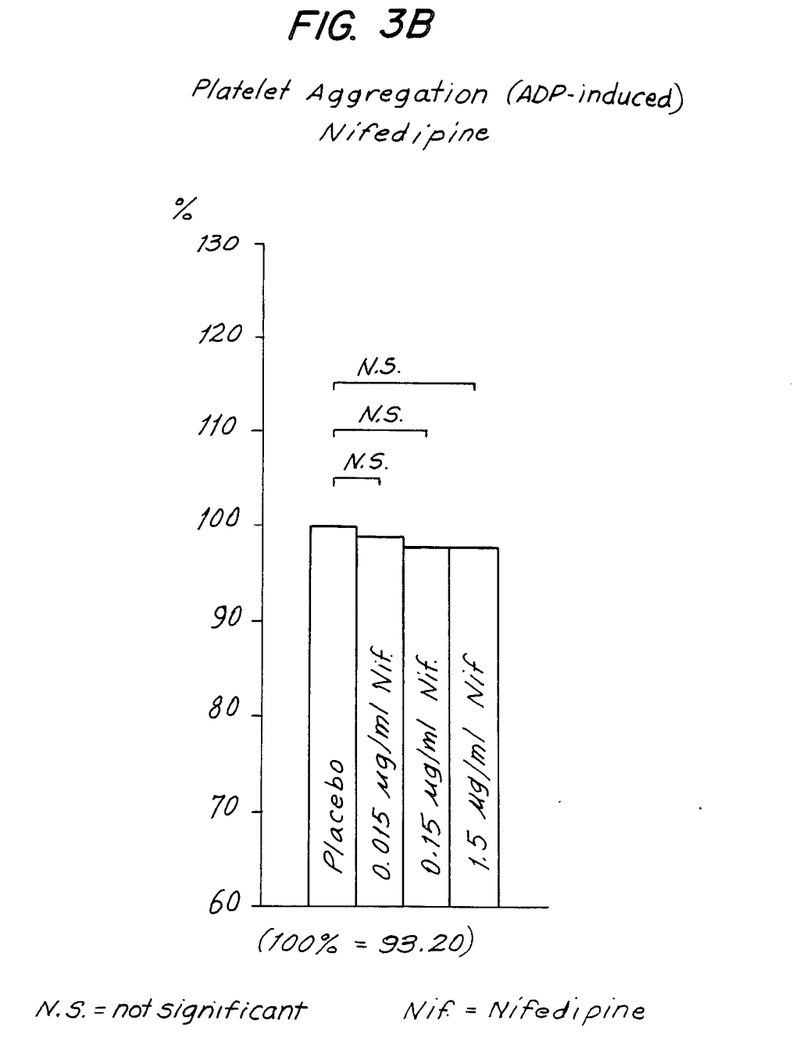
FIG. 3B is a graph illustrating the thrombocyte aggregation of a probe containing only Nifedipine.
Figure 3C:
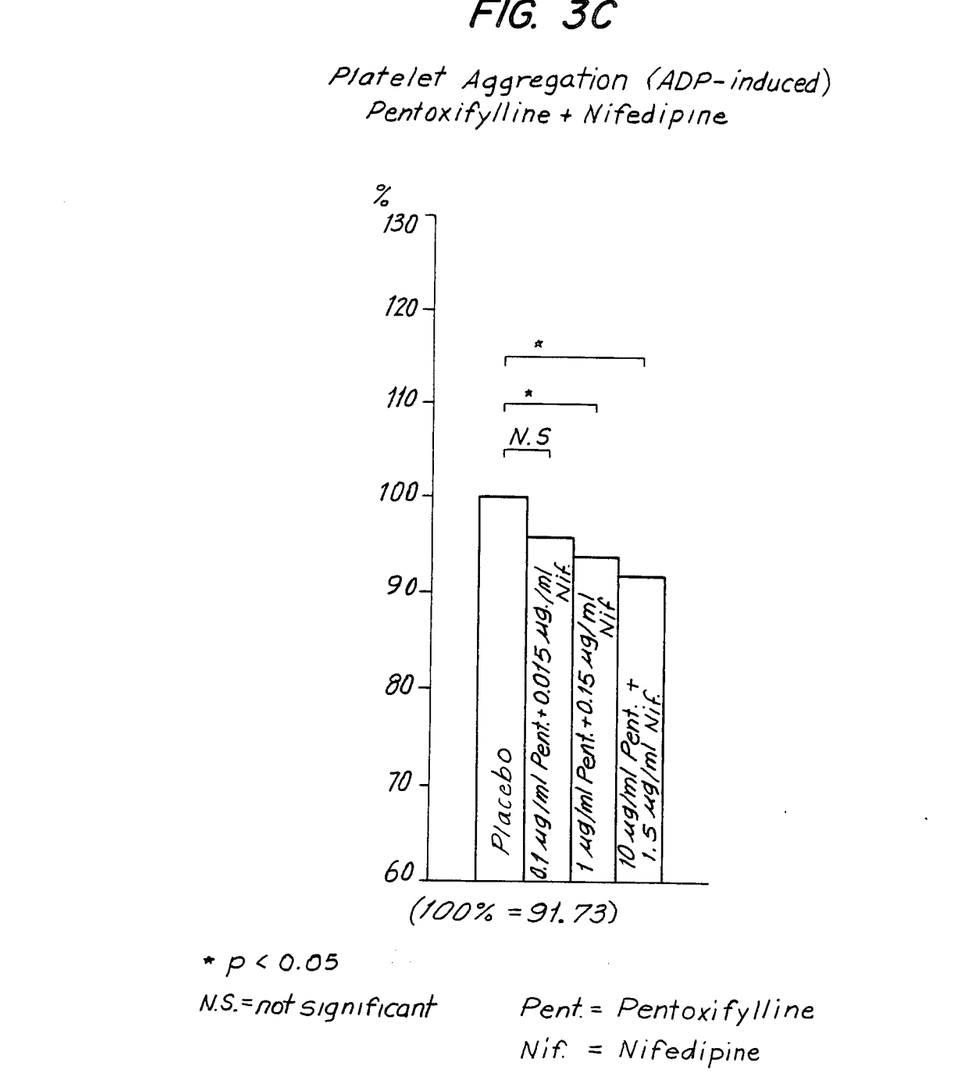
FIG. 3C is a graph illustrating the thrombocyte aggregation of a probe containing both Pentoxifylline and Nifedipine in accordance with the present invention.

Evaluation of the Results:

The percentages indicated in FIGS. 1A to 2C indicate the aggregates of erythrocytes and in FIGS. 3A to 3C the aggregates of thrombocytes. The letter "p" is an indication of the examination for significance which, for example, in FIG. 1A means that the result obtained is 95% significant.

1. Erythrocyte Flexibility

FIG. 1A shows that Pentoxifylline by itself resulted in a slightly significant ($p < 0.05$) increase in the erythrocyte flexibility as compared with the plaoebo specimen only at a concentration of 10 μg/ml of specimen.

Nifedipine by itself, FIG. 1B, led to the same effect only at the highest concentration of 1.5 μg/ml.

FIG. 1C shows that the combination of Nifedipine and Pentoxifylline results in a highly significant ($p < 0.01$) increase of the erythrocyte flexibility even at a concentration which is lower by a power of 10 than the highest concentrations of the individual components.

2. Erythrocyte Aggregation

FIG. 2A shows that Pentoxifylline by itself induces the inhibition of aggregation at a concentration of 10 μg.ml ($p < 0.05$).

Nifedipine by itself, FIG. 2B, did not show any aggregation-inhibiting effect at the concentrations examined. On the contrary, an increase in the tendency towards aggregation was measured.

FIG. 2C shows that even the medium concentration of the combination causes a significant reduction of the erythrocyte aggregation and the highest concentration results in a highly significant ($p < 0.01$) reduction.

3. Thrombocyte Aggregation (ADP-induced)

FIG. 3A shows that only the highest Pentoxifylline concentration of 10 μg/ml results in a highly significant ($p<0.01$) decrease of the thrombocyte aggregation as compared with the placebo and the other concentrations.

Upon the administration of Nifedipine alone, FIG. 3B, no significant effect was measured at any of the concentrations examined. Only the combination of Pentoxifylline and Nifedipine, FIG. 3C, shows already at the medium concentrations, a significant decrease of the thrombocyte aggregation as compared with placebo.

The results obtained with the various combinations of active substances show significant improvements of the parameters tested even in doses at which the individual active substances are not effective, or are only weakly effective. Even at the lowest concentrations of the combination of active substances, representing concentrations such as occur in vivo as subtherapeutic plasma level, relevant effects are noted.

The results clearly show that with the combination preparation according to the present invention, demonstrated by using as example the combination of the dihydropyridine Nifedipine with Pentoxifylline, a therapeutically relevant improvement in the parameters measured as compared with the individual substances is achieved. The result has a direct influence on the improvement of the blood flow properties which, as described at the beginning, intervene causally in the pathogenesis of the various severe symptoms. Additionally, it is particularly important that the concentrations of the combination preparation of the active substances can be clearly lower than the individual doses with their concomitant side effects, thereby enabling a long-term therapeutic administration with reduced load on the organism.

It will be understood that various changes may be made in the specific techniques and compositions described herein above without departing from the scope of the invention. Accordingly, preceding description is intended as illustrative only, the scope of the invention being determined solely by the claims appended hereto.

We claim:

1. A pharmaceutical composition comprising:
    (a) as active substance (A), Nifedipine having a calcium antagonistic effect; and (b) as active substance (B), Pentoxifylline, the quantity ratios of the active substances (A) and (B) being from about 1.10 to about 1:5.

2. The pharmaceutical composition of claim 1, wherein the active substances are present jointly as fixed combination in forms of supply for rectal, oral or parenteral administration.

3. The pharmaceutical composition of claim 1, wherein the active substances are present in similar, separate pharmaceutical forms for substantially simultaneous administration.

4. The parmaceutical composition of claim 1, wherein the active substances are present in separate, different pharmaceutical forms for substantially simultaneous administration.

5. A method for reducing erthyrocyte aggregation comprising administering to a patient an amount thereapeutically effective for reducing erythrocyte aggregation and at substantially the same time as active substances (A) Nifedipine having calcium-antagonistic effect; and as active substance (B) Pentoxifylline, the quantity ratios of the active substances (A) and (B) being from about 1:10 to about 1:5.

6. The method of claim 5, wherein the active substances (A) and (B) are concurrently administered.

7. The method of claim 5, wherein the active substances (A) and (B) are administered sequentially.

* * * * *